(12) United States Patent
Wilmot et al.

(10) Patent No.: US 7,569,035 B1
(45) Date of Patent: Aug. 4, 2009

(54) AUTOMATIC INJECTOR WITH ANTI-CORING NEEDLE

(75) Inventors: John G. Wilmot, Mount Airy, MD (US); John Whittier, Columbia, MD (US); Robert L. Hill, Abington, MD (US); Seth P. Cain, Baltimore, MD (US); C. Michael Mesa, Boyds, MD (US)

(73) Assignee: Meridian Medical Technologies, Inc., Columbia, MD (US)

(*) Notice: Subject to any disclaimer, the term of this patent is extended or adjusted under 35 U.S.C. 154(b) by 1118 days.

(21) Appl. No.: 09/985,466

(22) Filed: Nov. 2, 2001

(51) Int. Cl.
*A61M 5/00* (2006.01)
(52) U.S. Cl. .................................................. 604/187
(58) Field of Classification Search ............ 604/82, 604/83, 86–88, 134–138, 187, 200, 201, 604/203, 205, 264, 272, 274
See application file for complete search history.

(56) References Cited

U.S. PATENT DOCUMENTS

| | | | |
|---|---|---|---|
| 648,858 A | 5/1900 | Dolge | |
| 2,590,895 A | 4/1952 | Scarpellino | |
| 2,634,726 A | 4/1953 | Hanson | |
| 2,711,733 A | 6/1955 | Jacoby, Jr. | |
| 2,737,948 A * | 3/1956 | Brown | 604/192 |
| 2,745,403 A | 4/1956 | Goldberg | |
| 2,746,454 A * | 5/1956 | Sorensen | 604/272 |
| 2,748,769 A | 6/1956 | Huber | |
| 2,936,756 A | 5/1960 | Gabriel | |
| 3,492,992 A | 2/1970 | Kurtz | |
| 3,788,119 A | 1/1974 | Arrigo | |
| 3,924,617 A * | 12/1975 | Ferro | 604/411 |
| 4,381,779 A | 5/1983 | Margulies | |
| 4,394,863 A * | 7/1983 | Bartner | 604/90 |
| 4,413,993 A | 11/1983 | Guttman | |
| 4,490,139 A * | 12/1984 | Huizenga et al. | 604/57 |
| 4,537,593 A | 8/1985 | Alchas | |
| 4,661,098 A | 4/1987 | Bekkering et al. | |
| 4,808,170 A | 2/1989 | Thornton et al. | |
| 4,826,489 A | 5/1989 | Haber et al. | |
| 4,889,529 A | 12/1989 | Haindl | |
| 4,968,302 A | 11/1990 | Schluter et al. | |

(Continued)

FOREIGN PATENT DOCUMENTS

DE 42 26 476 C1 8/1993

(Continued)

*Primary Examiner*—Nicholas D Lucchesi
*Assistant Examiner*—Aarti Bhatia
(74) *Attorney, Agent, or Firm*—Jones Day; Garry J. Tuma

(57) ABSTRACT

In one embodiment, an automatic injector comprises a cartridge adapted to contain a charge of medicament, a seal structure disposed toward a forward end of the cartridge, a plunger normally disposed in a generally rearward end of the cartridge and movable through the cartridge toward a generally forward end thereof in response to an actuating procedure. The movable plunger rearwardly confines the medicament within the cartridge. A needle normally disposed in communication with the medicament container provides a passage in which the medicament is released into an individual's flesh in response to an actuating procedure projecting the needle into the flesh of the individual. The cartridge having an increased friction region so as to slow the motion of the plunger when the forward end of the needle travels through the seal in order to eliminate coring.

32 Claims, 16 Drawing Sheets

U.S. PATENT DOCUMENTS

| | | | |
|---|---|---|---|
| 4,969,877 A | | 11/1990 | Kornberg |
| 5,102,393 A | | 4/1992 | Sarnoff et al. |
| 5,290,267 A | * | 3/1994 | Zimmermann .............. 604/272 |
| 5,354,286 A | * | 10/1994 | Mesa et al. ................. 604/230 |
| 5,391,151 A | | 2/1995 | Wilmot |
| 5,533,993 A | | 7/1996 | Maier |
| 5,575,780 A | * | 11/1996 | Saito .......................... 604/272 |
| 5,709,668 A | | 1/1998 | Wacks |
| 5,716,348 A | | 2/1998 | Marinacci et al. |
| 5,820,609 A | * | 10/1998 | Saito .......................... 604/272 |
| 5,968,022 A | * | 10/1999 | Saito .......................... 604/272 |
| 6,004,300 A | | 12/1999 | Butcher et al. |
| 6,213,989 B1 | * | 4/2001 | Utterberg .................... 604/272 |
| 6,626,887 B1 | * | 9/2003 | Wu ............................. 604/512 |
| 6,702,791 B1 | * | 3/2004 | Hilgers et al. ............... 604/274 |
| 7,070,583 B1 | * | 7/2006 | Higuchi et al. .............. 604/274 |
| 2008/0154217 A1 | * | 6/2008 | Carrez et al. ................ 604/272 |

FOREIGN PATENT DOCUMENTS

| | | |
|---|---|---|
| EP | 1 090 651 A1 | 4/2001 |
| FR | 1225009 | 6/1960 |
| WO | WO 92/20388 | 11/1992 |
| WO | WO96/39213 | 12/1996 |
| WO | WO 01/23020 A2 | 4/2001 |

* cited by examiner

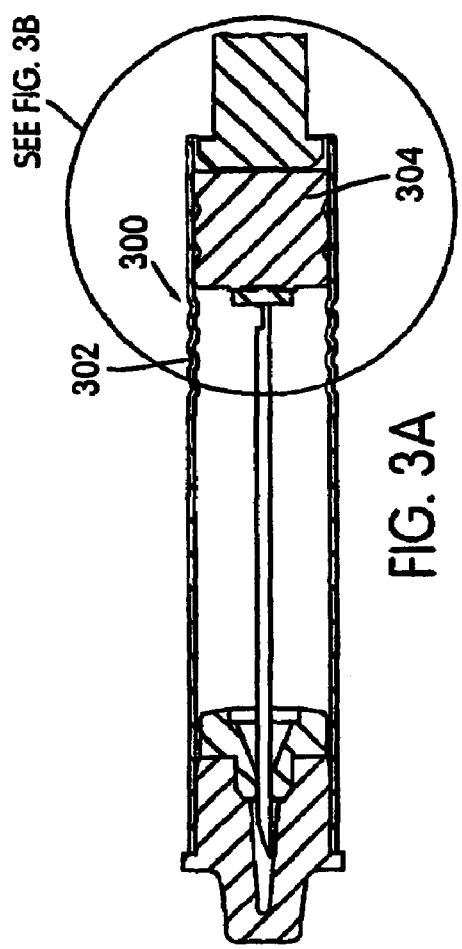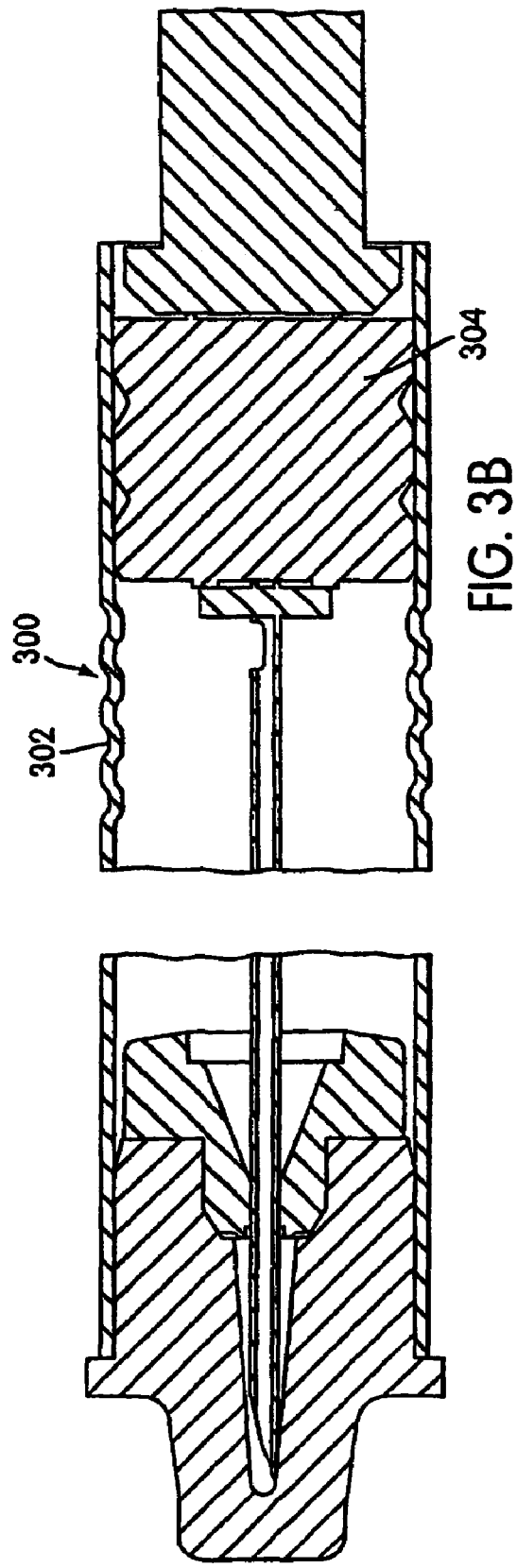

AUTOMATIC INJECTOR WITH ANTI-CORING NEEDLE

BACKGROUND

1. Field of Invention

The present invention relates to automatic injectors, and more particularly, to automatic injectors that reduce the likelihood of coring a sealing member.

2. Discussion of Related Art

Automatic injectors are well known. Basically an automatic injector is a device for enabling an individual to self-administer, or administer to another, a dosage of a liquid medicament. An advantage of automatic injectors is that they contain a measured dosage of a liquid medicament in a sealed sterile condition capable of storage in such condition for an extensive period of non-use, during which period immediate injection of the stored dosage may be accomplished at any time under severe emergency conditions. Another advantage of automatic injectors is the administration of the self-contained dosage of liquid medicament is accomplished without the necessity of the user initially seeing the hypodermic needle through which the liquid medicament is injected or of manually penetrating such visible needle into the user's or another person's tissue.

As stated above, automatic injectors are particularly suited for use under emergency conditions. For example many tens of millions of such automatic injectors have been manufactured and sold containing nerve gas antidotes for use under emergency chemical warfare conditions. Typical units which have been utilized for this purpose are disclosed in U.S. Pat. Nos. 2,832,339, 3,882,863, and 4,031,893. In addition units of this type have been manufactured and used in administering anti-arrhythmic medicaments under emergency conditions relating to hart attack medical situations. The use of an auto injector has also been proposed to provide other medicaments useful in treating heart attack symptoms such as clot selective thrombolic agents (for example, tPA) and related medicaments. See for example, U.S. Pat. Nos. 4,689,042, 4,755,169, and 4,795,433. In addition, automatic injectors have been widely marketed containing a dosage of epinephrine as an antidote for counteracting severe allergic reactions, as for example, to bee stings, and the like.

In all of these instances, the auto-injector is specifically structured so that in its normal operation the needle extends into the tissue of the individual and a specified amount of liquid medicament stored in a cartridge within the injector is injected into the tissue of the individual.

The hypodermic needle of an autoinjector has a forward end adapted to penetrate the clothing and flesh of an individual and a rearward end adapted to communicate with a liquid medicament source so that the medicament is permitted to flow from the source, through the central longitudinal bore or lumen in the needle, and into the flesh of the individual. In some embodiments, the needle is contained inside the cartridge containing the liquid medicament. For example one application exists in the field of automatic injection devices, wherein the liquid medicament is sealed within a tubular container or cartridge, generally made of glass, plastic or metal, having a rubber seal closing off at the forward end and a rubber plunger at the rearward end. For example see U.S. Pat. No. 5,354,286. During an injection operation, a stressed spring assembly is released moving a push rod against the plunger. The plunger pushes against the hub-end of the needle causing the needle to puncture the forward end seal of the cartridge and penetrates into the flesh of an individual. The liquid medicament is pushed at the same time through the needle, thus releasing the medicament into the individual's flesh.

In another type of automatic injector, the needle is connected to the forward end of the cartridge. See U.S. Pat. No. 5,102,393. During an injection operation, the needle is forced through a resilient seal at the forward end of the outer housing or through an elongated rubber sheath surrounding the needle. In either case the needle is kept sterile by a seal disposed toward a forward end of the housing while the injector is stored. After the needle punctures the seal or sheath, it then is forced into the flesh of the individual.

An issue that must be dealt with in each of the mentioned arrangements is that the forward end of the needle must perforate a rubber or other type of seal, and it is possible for the forward end of the needle to core out or dislodge a small particle of material from the seal and potentially block the needle orifice/lumen or be forced into the individual's flesh.

SUMMARY OF INVENTION

To overcome these problems and others, it is proposed to provide an automatic injector in which the amount of coring by the needle is substantially reduced or eliminated.

Therefore, in one embodiment of the present invention is to provide an automatic injector that comprises: a housing; a seal structure disposed toward a forward end of the housing; a cartridge contained within the housing; a charge of medicament contained in the cartridge; a plunger normally disposed in a generally rearward end of the cartridge and movable through the cartridge toward a generally forward end thereof in response to an actuating procedure. The movable plunger rearwardly confines said medicament within said cartridge. A needle is normally disposed within the housing, the needle being projectable from a forward end of said housing through said seal structure. The needle is communicable with the medicament so that movement of the plunger through the cartridge forces the medicament through the needle and into the flesh of an individual, in response to the predetermined actuating procedure. A releasable energy source is releasable in response to the predetermined actuating procedure to project the needle from the forward end of the housing and slidingly drive the plunger through the cartridge in sealed relation to expel the medicament through the needle and into the flesh of an individual. The cartridge has an increased friction region so as to slow the motion of the plunger as the forward end of the needle travels through the seal.

In another embodiment, the needle carries a damping structure for reducing the rate of acceleration of the needle by the resistance created when said damping structure moves within said medicament.

In addition, the present invention is directed to several automatic injection devices comprising novel needle structures that reduce coring of an elastic, plastic or rubber based structure at the forward end of the injector.

BRIEF DESCRIPTION OF THE DRAWINGS

These and other objects and advantages of the invention will become more apparent and more readily appreciated from the following detailed description of the presently preferred exemplary embodiments of the invention, taken in conjunction with the accompanying drawings, of which:

FIG. 3 is a longitudinal sectional view of the cartridge showing the friction region according to an alternative embodiment of the present invention;

DETAILED DESCRIPTION OF PREFERRED EMBODIMENT

In the following description, for purposes of explanation and not limitation, specific details are set forth such as particular shapes and materials, mechanical components, techniques, etc. in order to facilitate a thorough understanding of the present invention. However, the invention may be practiced in other embodiments that depart from these specific details. The terms "damping structure", "friction area", "speed bump" and "narrowed diameter portion" are used interchangeably in this description to illustrate a feature that is used as a way to reduce the rate of acceleration thus decrease the speed at which the hypodermic needle punctures or pierces the forward seal in comparison with prior art auto-injectors. Also, for the purpose of this disclosure, the portions of the injector on the right side of FIG. 1 (on the needle extension end) will be considered the front end, while the left side or activation end will be considered the rear end.

Figure 1:
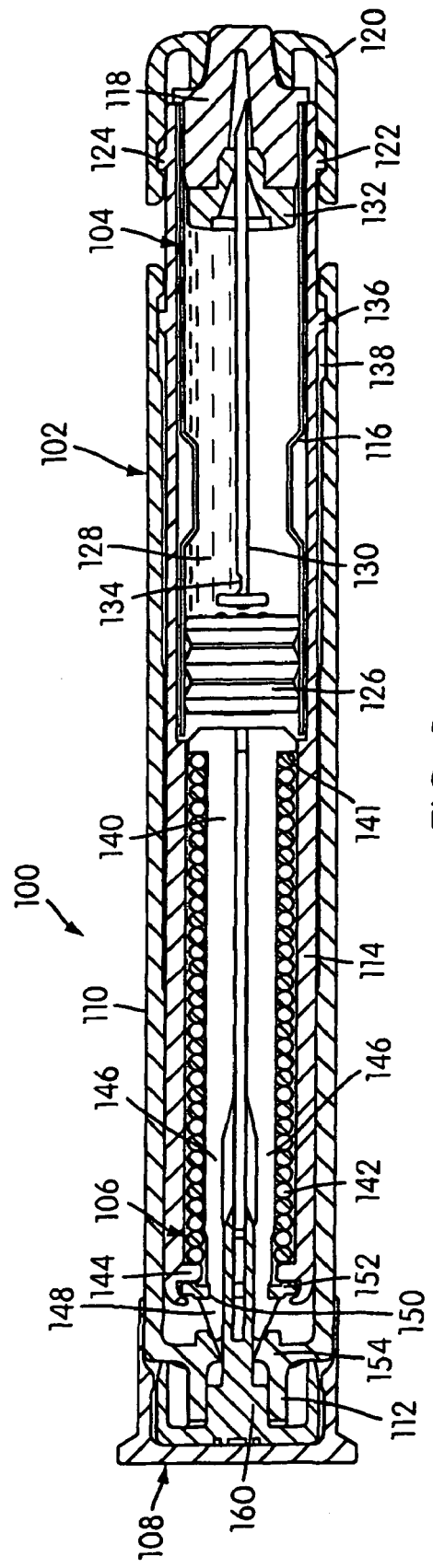
FIG. 1 is a longitudinal sectional view of an automatic injector according to an embodiment of the present invention.

Referring, more particularly, to the drawings in detail, there is shown in FIG. 1 an automatic injector 100. The automatic injector 100 includes a tubular housing 102, a medicament cartridge assembly 104, within the forward end portion of the housing assembly 102, and a releasable energy source 106 which is releasable in response to a predetermined actuating procedure as will be described in detail in the following paragraphs. While the releasable energy source can be any type of assembly which effectuates an injection operation, such as a compressed gas assembly as disclosed in U.S. Pat. No. 4,518,384, it is preferred that the releasable energy source be a stressed spring assembly, as generally indicated at 106. The stressed spring assembly is disposed within the rearward end portion of the housing assembly 102 in operative relation with the medicament cartridge assembly 104. A releasable end safety cap 108 positioned at the rear of the housing assembly 102 is in operative relation with the stressed spring assembly 106.

The housing assembly 102, medicament cartridge assembly 104, and stress spring assembly 106 are generally constructed in accordance with the teaching of U.S. Pat. No. 2,832,339, hereby incorporated by reference. As shown in FIG. 1, the housing assembly 102 includes a cylindrical outer housing member 110 having a centrally apertured cylindrical rear wall portion 112 of reduced diameter on which the safety end cap 108 is mounted. The housing assembly 102 also includes an inner cylindrical housing member 114 within the housing member 110 within which is mounted the medicament cartridge assembly 104 and the stressed spring assembly 106. The forward portion of the inner housing member 114 is formed with a counterbore for receiving therein a cylindrical dosage container or cartridge 116 of the medicament cartridge assembly 104. The cartridge of the present invention is preferably made of metallic materials such as, but not limited to, stainless steel and aluminum. Other materials, such as plastic materials (e.g., polypropylene) or glass are also within the scope of the present invention.

The forward end of the container or cartridge 116 is closed by a stopper or seal 118, preferably, of suitable rubber or compliant plastic material. The cartridge assembly 104 is retained in closing relation with the forward end of the inner housing member 114 by a housing end cap member 120 of molded plastic material. The cap 120 is preferably retained on the inner housing member 114 by inter-engagement of a pair of ridges 122 formed on the exterior periphery of the tubular member 114 with an annular groove 124 formed on the interior periphery of the cap member 120. The rearward end of the cartridge 116 is closed by a rubber or plastic plunger 126 which is slidably, sealingly engaged with the inner surface of cartridge 116 so as to enclose within the cartridge a dosage 128 of a liquid medicament.

A hypodermic needle 130 is disposed within the cartridge 116. It thus can be appreciated that the cartridge assembly 104 includes cartridge 116, seal 118, needle 130 and disc 132. As can be discerned from FIG. 1, needle 130 is normally stored in contact with the medicament 128. However, in the broadest aspects of the present invention, it can be appreciated that needle 130 can be disposed in a separate chamber (either evacuated or filled with a preferably inert gas) forwardly of the medicament 128 (for example, see our U.S. Pat. Nos. 5,085,642 and 5,102,393), so long as the needle is somehow communicable with the medicament in a manner which permits the medicament to travel through the needle and into the flesh of an individual. The needle can also be disposed in contact with one of two medicaments, which are normally stored separately within the injector and then either mixed within the injector prior to an injection (e.g. see U.S. Pat. No. 5,041,088) or injected separately one after the other (see U.S. Pat. No. 5,092,843). The hypodermic needle 130 is preferably made from stainless steel.

In the present embodiment, the needle 130 has its pointed end disposed within a recess formed in the seal 118. A disc 132 of plastic is disposed within the forward end of the cartridge 116 in surrounding, securing and guiding relation with the hypodermic needle 130 and in abutting engagement with the seal 118. The disc 132 serves to releasably hold the needle in its storage position to provide peripheral centering therefore during the dosage injecting stroke of the plunger 126. The rearward end of the hypodermic needle 130 is enlarged for engagement by the plunger and has a slot 134 formed in its side wall adjacent the enlarged end for communicating the dosage 128 with the hollow interior of the hypodermic needle 130 when the plunger 126 is in engagement therewith. The inner housing member 114 is mounted within the outer housing member 110 for limited reciprocating movement as determined by a pair of ridges 136 formed on the exterior periphery of the tubular inner housing member 114 at a position spaced rearwardly from the pair of ridges 122. The pair of ridges 136 is adapted to engage with an elongated annular groove 138 formed on the interior periphery of the outer housing member 110.

The stressed spring assembly 106 includes a normally compressed but releasable coil spring 142 and an elongated collet member 140. The collet member is disposed within the rearward portion of the housing member 114 and has its forward end disposed adjacent to the plunger 126. The forward end of the collet member 140 has a flange 141 configured to engage the forward end of the stressed coil spring 142, which surrounds the central portion of the elongated collet member 140. The collet 140 has its rearward end engaged with a locking ring 152 sitting on an annular end flange 144 formed integrally on the rearward end of the inner housing member 114.

The rearward end of the elongated collet member 140 are split to provide a plurality (e.g., four) flexible spring fingers 146, the rearward extremities of which are formed with rearwardly and outwardly facing cam releasing surfaces 148. Extending inwardly from the rearward end of each cam surface 148 is locking shoulder 150 adapted to engage a locking ring 152 seated on the rear surface of flange 144. The forward portion of the apertured cylindrical wall portion 112 is formed with a complementary cam surface 154, which is disposed in engagement with the cam surfaces 148 so as to effect a laterally inward movement of the spring fingers 146 toward one another to disengage locking shoulders 150 from locking ring 152 in response to a relative forward actuating movement of the outer housing member 110 with respect to the inner housing member 114. This inward action of the spring fingers 146 is permitted only after the safety cap 108 is removed, as will be described.

The operation of the injector will now be described. In the first step of operation, releasable end cap 108 is removed from the injector 100. This removal is accomplished simply by gripping the exterior periphery of the end cap 108 and moving it rearwardly while gripping and holding the outer housing member 110. The cap member 108 carries with it a safety pin portion 160. With the safety pin portion 160 removed from its safety position, which normally prevents the laterally inward movement of the spring fingers 146, the user can now complete the operation by moving the forward cap member 120 into contact with the tissue of a person to be injected. By applying a continued forward force on the exterior periphery of the outer housing member 110, cam surfaces 154 thereof are moved forwardly. This forward movement in cooperation with the cam surfaces 148 on the spring fingers 146 causes the locking surfaces 150 of the latter to move inwardly off of the locking ring 152, thus releasing the stressed spring 142. The spring 142 acts through the collet member 140 to move the same forwardly which has the effect of moving the plunger 126 with it. As the plunger moves forwardly, it carries with it the needle 130. The pointed forward end of the needle pierces through the seal 118 and into the tissue of the patient. At the same time, the dosage 128 of liquid medicament within the cartridge 116 is caused to move inwardly into the slot 134 of the needle and outwardly of the pointed forward end thereof as the same moves into the tissue of the user.

Figure 2A:
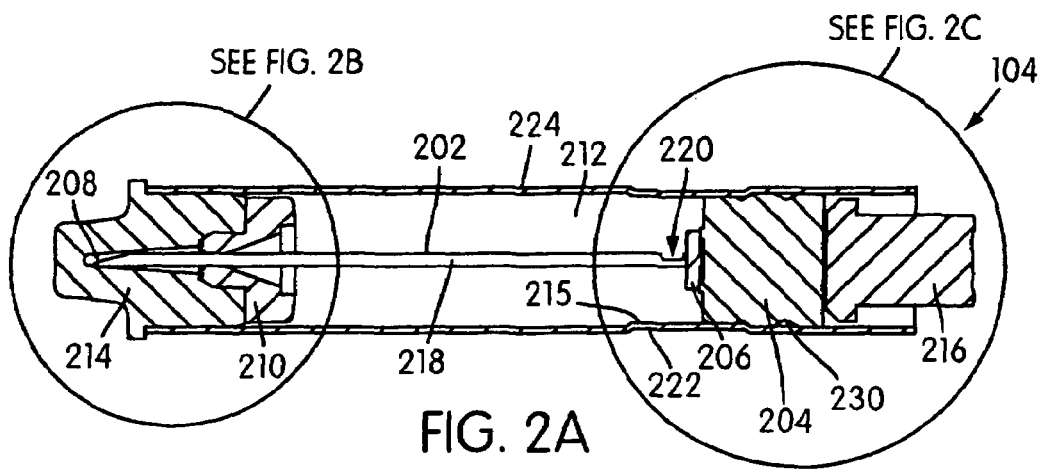
FIG. 2 is a longitudinal sectional view of a cartridge showing the friction region according to an embodiment of the present invention.
Figure 2B:
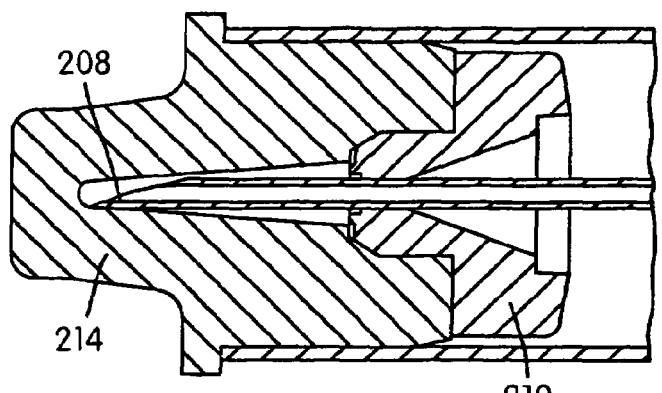

Referring more particularly to FIG. 2A, describing in more detail the cartridge assembly 104. The hypodermic needle 202 comprises an elongated tube, generally cylindrical terminated at the rearward end by hub 206. The forward end of the needle has a pointed shape 208, shown in more detail in enlarged FIG. 2B. The needle 202 is maintained along a longitudinal axis X with holder 210. Needle 202 is shown housed inside cartridge 212, containing a liquid medicament. However as stated previously needle 202 need not be inside cartridge 212 but can be arranged to be outside the medicament cartridge. The forward end of cartridge 212 is terminated by seal 214 to keep the liquid medicament from leaking, shown in more detail on FIG. 2B. The pointed end 208 of needle 202 is oriented toward seal 214. Therefore, initially the needle 202 is disposed between plunger 204 and seal 214. The plunger is shown in this figure as a one piece material, however it is understood that the plunger can be made of a plurality of pieces with various ductile constants such as a harder piece and a softer piece of rubber.

Seal 214 is made of a flexible material, such as but not limited to, rubber. It is known that polymers behave in a ductile manner when strained at low speed and behave in a brittle manner when strained at high speed.

In order to substantially reduce or eliminate coring, the needle 202 is arranged to penetrate in a "gentle" manner into the rubber seal 214 by reducing the thrust of the needle. Cartridge 104 has a friction region 215 for slowing the motion of plunger 204 thus reducing the rate of acceleration of needle 202 when perforating seal 214. The acceleration rate is reduced so that the speed of the needle is less than 680 inches/s when the needle pierces the seal. The reduction in acceleration rate is intended specifically to reduce the speed to a level at which coring will not occur. Preferably, the speed at which the seal is pierced is also greater than 150 inches/s so that the injection operation is not delayed more than what is desirable. The friction region in this embodiment is a narrowed diameter portion or localized narrowed diameter portion 222 in the wall 224 of cartridge 212. The narrowed diameter portion 222 also referred to as speed bump is arranged between seal 214 and plunger 204. The narrowed diameter portion 222 is arranged and configured to reduce acceleration of plunger 204, thus reducing the speed at which the needle 202 would otherwise travel when the needle tip 208 travels through seal 214. The narrowed diameter portion 222 is created on the wall of the cartridge 212 with a pressure forming method, for example with a clamshell die. The die or a rolling process can be used to imprint a selected shape to the stainless wall of cartridge 212. For example cylindrical rounded narrowed diameter portion around the cylindrical wall of the cartridge can be imprinted.

The localized narrowed diameter portion 222 in the wall 224 of cartridge 212 acts as a "speed bump" by slowing down the motion of plunger 204. Indeed, the narrowed diameter portion 222 increases the normal force between the plunger periphery and the wall 224 of cartridge 212, thus creating a frictional force counter to the plunger's movement. The narrowed diameter portion 222 increases the diametrical interference thereby increasing the friction and retarding plunger 204 movement. This slowed movement causes the needle 202 to strain the seal 214 in a more ductile mode, thus leading to a substantial reduction in coring.

The speed bump is arranged to be only effective along a partial length of the cartridge 212. This allows the plunger to receive the full spring force at the beginning of operation helping to overcome static friction between the plunger 204 and the cartridge 212. The speed bump then takes effect immediately prior to the front end of the needle contacts the seal 214. After the needle tip 208 completes its penetration of the seal 214, the speed bump disengages making the full spring force available to ensure completeness of the injection process.

Figure 2C:
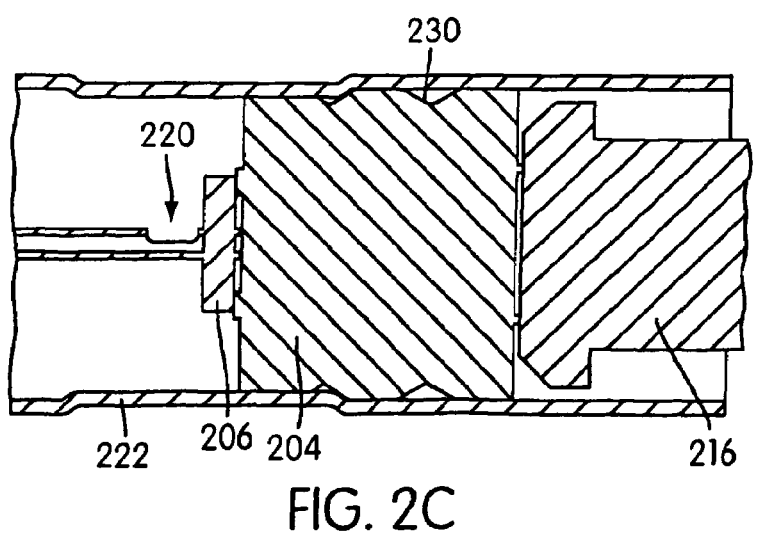

The plunger 204 meets increased resistance when the plunger 204 reaches the narrowed diameter portion 222. Plunger 204 has a plurality of ribs 230 as shown in FIG. 2C. Each time a rib 230 of the plunger 204 encounters an edge of narrowed diameter portion 222 the friction force is increased thus leading to a net decrease in injection acceleration rate.

In another embodiment, illustrated in FIG. 3A, the friction region 300 comprises a corrugated configuration comprising a plurality of projections 302, shown enlarged in FIG. 3B, in order to multiply the interference with the plunger 304.

It is to be understood however, that friction region 300 can be any structure of the cartridge that slows plunger 304. While in the embodiments shown it is the wall of the cartridge itself that performs this function, it should be appreciated that the cartridge may employ a separate structure inserted therein. The plunger 304 meets increased resistance when the plunger's leading rib crosses the friction region leading edge. The rippled shape of friction region 300 illustrated in FIG. 3 exchanges some of the aforementioned diameter decrease in the previous embodiment in exchange for a multitude of leading edges.

To demonstrate the effectiveness of the present invention in substantially reducing formation of cores, a series of tests are implemented and data is acquired.

Figure 4:
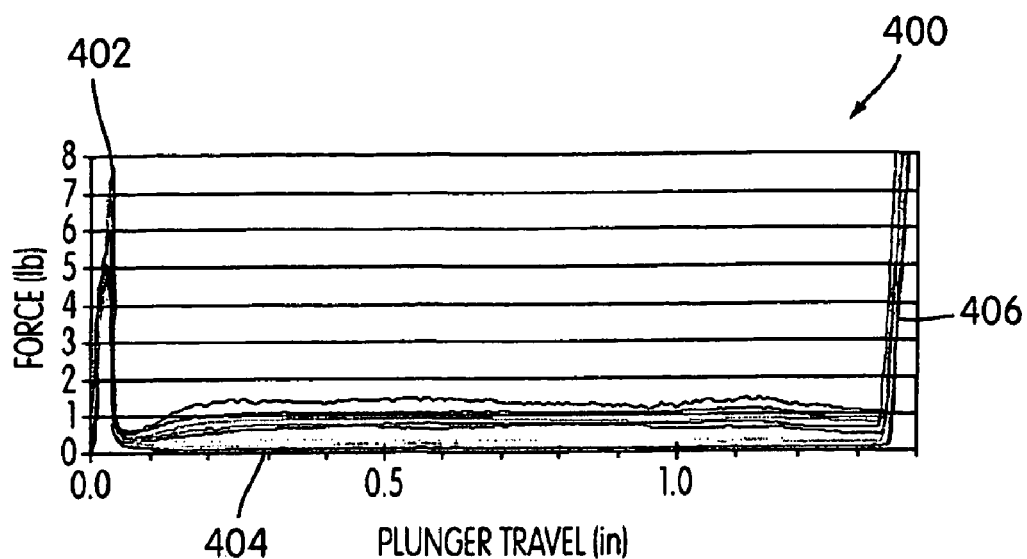
FIG. 4 is a graph showing the force versus distance of travel of plunger in a configuration without an increased friction region, as will be described hereinafter.

FIG. 4 shows the force-distance data profile of a standard cartridge-plunger. The curve 400 exhibits a high static friction spike 402 followed by a constant kinetic friction stage 404. Numerous tests are run to collect statistical data. The mean kinetic friction from the statistical data is determined to be 0.54 lb. The nearly vertical spike 406 at the terminus represents bottoming of the plunger against the seal.

Figure 5:
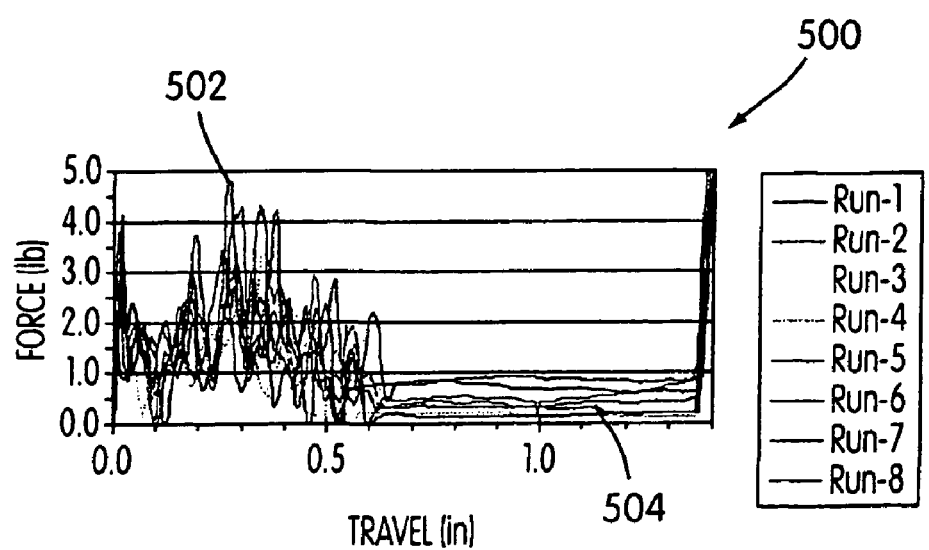
FIG. 5 is a graph showing the force versus distance of travel of plunger in a configuration when using embodiment illustrated in FIG. 3.

FIG. 5 shows the force-distance data profile of a cartridge having corrugated portion and a plunger, as illustrated in FIG. 3. The portion of travel in which the ripples are in effect is clearly visible on curve 500. The "spikiness" of data at the friction phase 502 is caused by the individual matings and separations of the individual ripples with plunger ribs. Similarly statistical data is acquired to allow calculation of the mean kinetic friction during the speed bump phase. The mean kinetic friction is determined to be 1.47 lb. The mean kinetic friction of the post speed bump phase, shown on FIG. 5 as phase 504, is 0.52 lb.

Figure 6:
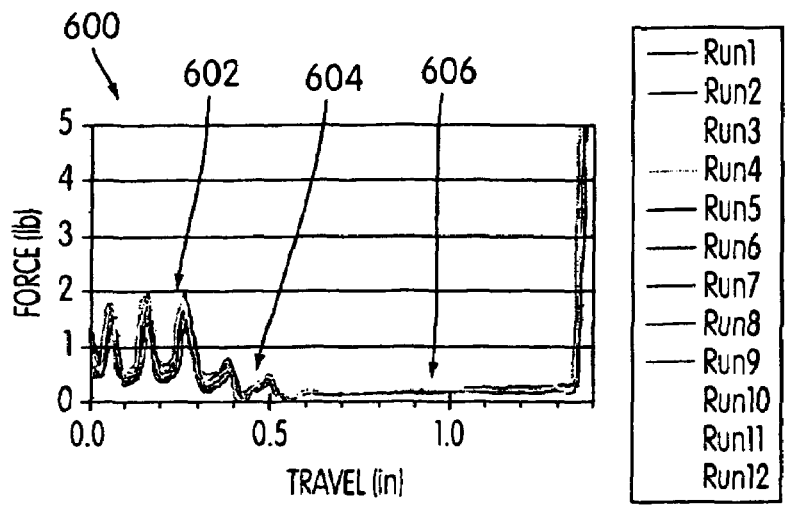
FIG. 6 is a graph showing the force versus distance of travel of plunger in a configuration when using embodiment illustrated in FIG. 2.

FIG. 6 shows the force-distance data profile 600 of a smooth speed bump and a plunger having three ribs, as illustrated in FIG. 2. The three large consecutive spikes 602 are caused by the three ribs of the plunger entering the speed bump. The smaller spikes 604 occur as the plunger's ribs exit the speed bump. Similarly statistical data is acquired to allow calculation of the mean kinetic friction during the speed bump phase. The mean kinetic friction during the speed bump phase is determined to be 1.71 lb. The mean kinetic friction of the post-speed bump phase, shown on FIG. 6 as phase 606, is similar to the data described previously.

Figure 7:
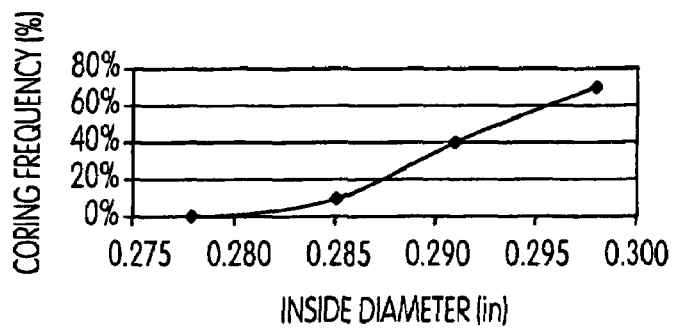
FIG. 7 is a graph showing the percentage of coring versus the inside diameter measured at an increased friction region, as will be described hereinafter.

Data is also acquired to demonstrate that the introduction of the speed bump reduces coring. FIG. 7 shows the coring frequency versus the inside diameter of the cartridge at the speed bump. The highest point on the curve corresponds to the inside diameter 0.298" of the cartridge without a speed bump. At this size (without a speed bump) approximately 70% of units tested produced cores. The lowest point on the curve corresponds to the smooth (without ridges) speed bump in its intended diameter of 0.278". Statistical data showed a population of less than 1% revealed coring.

In the case of a cartridge with a speed bump, a softer spring for pushing the plunger, may be used if desired to allow a smoother transition from the diameter of cartridge without the bump to the diameter of the cartridge at the bump.

Figure 8:
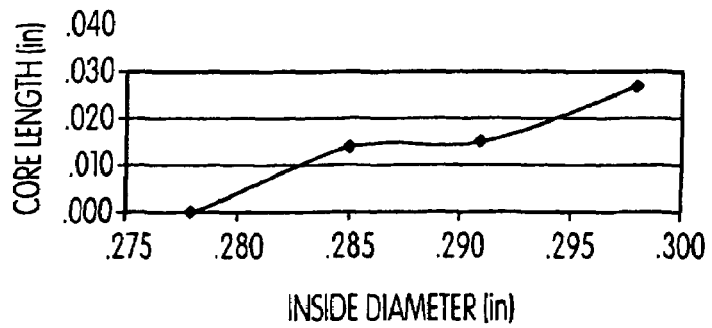
FIG. 8 is a graph showing the core length versus the inside diameter measured at an increased friction region, as will be described hereinafter.

In addition to coring frequency, the diameter of the particles generated by coring are also measured and reported in FIG. 8. As seen in FIG. 8, the dimension of the core (particle) decreases when the inside diameter of the cartridge at the speed bump decreases. Therefore, the speed bump has also an advantage in decreasing the size of the coring particles.

Figure 9:
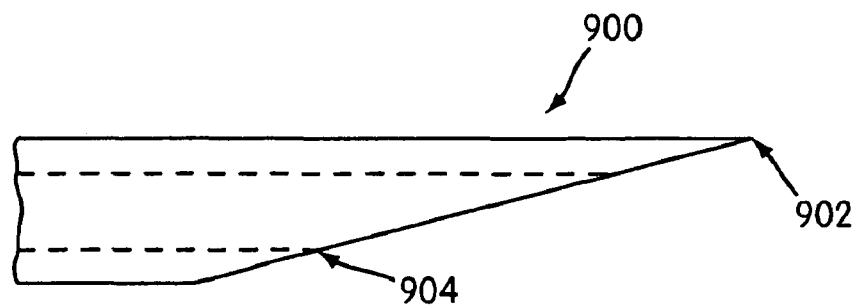
FIG. 9 is an enlarged view of a straight tip showing the point and the heel of the needle.

These tests are carried out for a straight tip needle such as shown in FIG. 9 (which is a simplified view of the needle of FIG. 3A). Needle tip 900 has generally a point 902 and a heel 904. As can be seen in the following embodiments the needle tip can have a curved shape instead of a straight shape as in FIG. 9.

Figure 10:
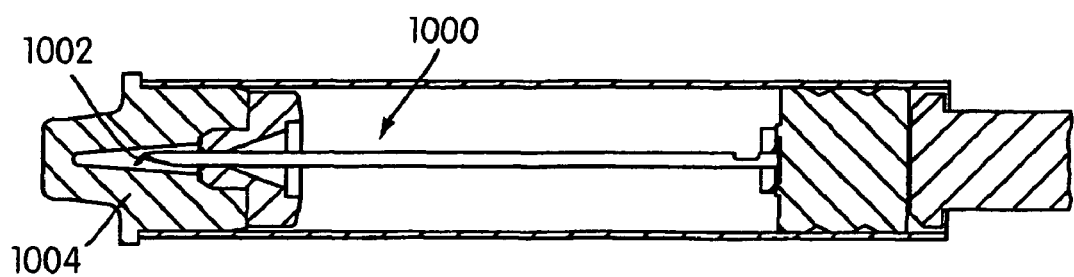
FIG. 10 is a longitudinal sectional view of the hypodermic needle as installed in a cartridge according to another embodiment of the present invention; the hypodermic needle is shown having a curved tip.
Figure 11A:
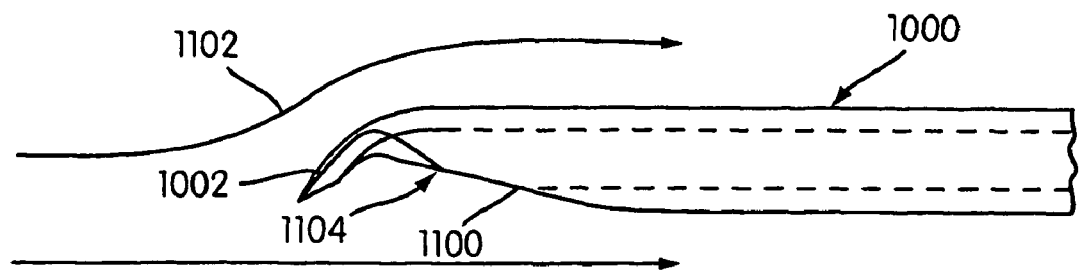
FIG. 11A is an enlargement of the tip of the needle according to embodiment illustrated in FIG. 10 having curved "C" tip.

FIG. 10 shows a longitudinal sectional view of the automatic injector with hypodermic needle according to another embodiment of the present invention. The hypodermic needle 1000 is shown having a curved tip 1002. As mentioned previously, and now illustrated in FIG. 11A, the curved leading edge 1002 of needle 1000 having a C-tip configuration pushes the material of the seal 1004 far enough away from the heel 1100 to prevent intimate contact. The curved arrow 1102 indicates the direction of flow of seal material relative to the movement of the needle 1000. The arrow indicates in particular that the seal material flows around the curved tip 1002. In other words, the curved tip 1002 acts as a shield for the orifice or lumen 1104 of needle 1000, by blocking the seal material 1004 from penetrating through the orifice 1104. The extent to which the needle tip is curved over the orifice influences seal coring frequency.

Figure 11B:
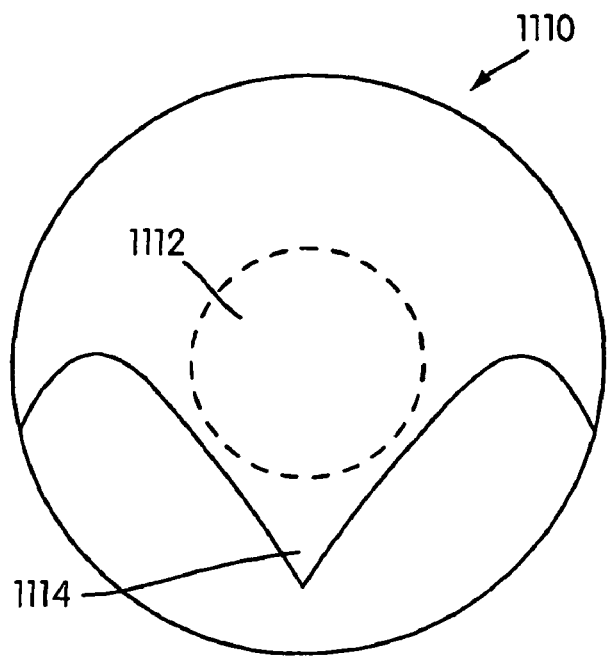
FIG. 11B is an enlargement frontal view of the pointed tip of the needle.

FIG. 11B shows an enlargement frontal view of the pointed tip 1110 of the needle. The curved forward tip 1114 is shown completely shielding lumen 1112 thus protecting lumen 1112 of being in direct contact with the seal material as previously discussed. In other words, the bent tip 1114 shields the entire cross-section of the longitudinal passage in the needle.

Figure 12:
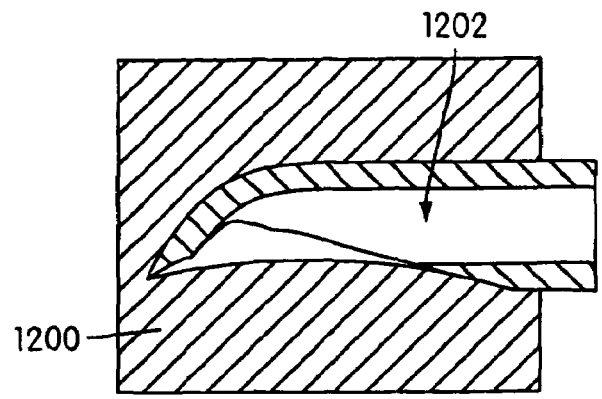
FIG. 12 is a longitudinal expanded sectional view of the forward end of the needle showing the interaction of the seal material with a curved tip needle having a regular/thinner wall thickness.
Figure 13:
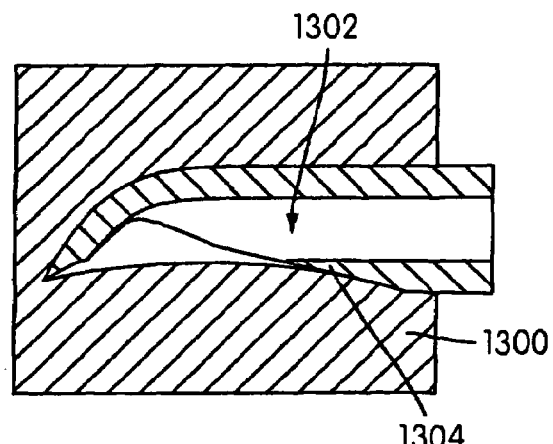
FIG. 13 is a longitudinal expanded sectional view of the forward end of the needle show the interaction of the seal material with a needle having a heavy/thicker wall thickness.

FIG. 12 shows the interaction of seal material 1200 with needle 1202 having a regular wall thickness, preferably between 0.0055 inch and 0.0065 inch. FIG. 13 show the interaction of seal material 1300 with needle 1302 having a thicker wall (heavy wall) preferably between 0.0083 inch and 0.0090 inch. In particular, FIG. 13 illustrates that in the case of needle with heavy wall thickness 1302, the heel 1304 is further away from the seal material 1300, thus further reducing coring potential compared to needle with regular wall thickness 1202. Testing shows that in the eventuality cores are produced, cores are generally smaller when using heavy-wall needles versus regular wall needles of similar geometry.

Figure 14:
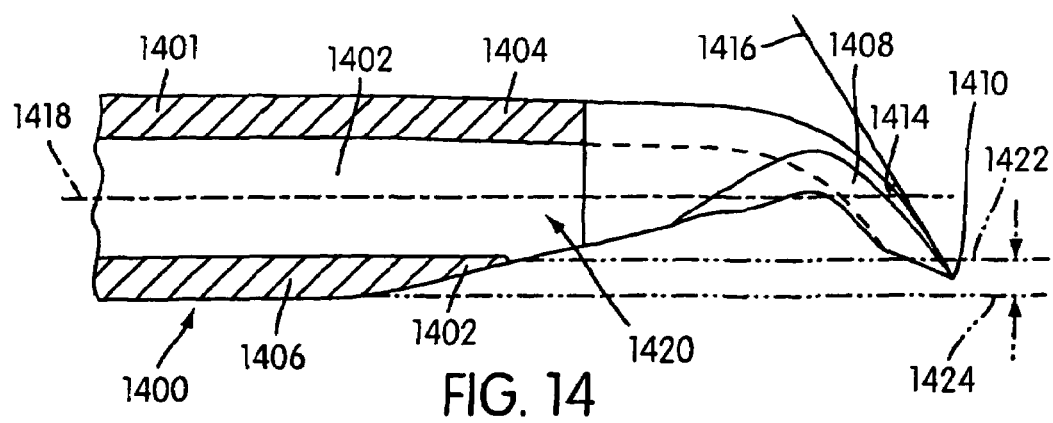
FIG. 14 is a longitudinal expanded sectional view of the forward end of the needle showing the curvature tolerance limits.

FIG. 14 shows the geometry of the C-tip needle 1400 with manufacturing limits for the hard C-tip geometry. The needle comprises a hollow rigid tubing 1401 having a cylindrical wall defining a longitudinal passage. The cylindrical wall includes first and second opposing wall portions. First wall portion is illustrated in this figure by longitudinal cross-section 1404 and second wall portion is illustrated in this figure by longitudinal cross-section 1406. The first wall portion 1404 has a forward tip portion 1408 terminating in a forward end tip 1410. The second wall portion 1406 terminating at a position 1412 rearwardly spaced from the end tip 1408. The forward tip portion 1408 is bent at angle 1414. Angle 1414 is defined as the angle between tangent 1416 to curvature of the outer surface at the end tip 1410 and the longitudinal axis 1418 of needle 1400. In one embodiment, the forward end tip 1410 terminates in a region defined by an imaginary forward extrapolation of the thickness of second wall 1406 defined by limits 1422 and 1424 which are intended to insure that the end tip 1410 is always deflected far enough to always shield the lumen or opening 1420, but not deflected so far to hinder the penetration or withdrawal of the needle (this applies equally to the embodiment of FIG. 17). Other C-tip geometry is the soft C-tip needle where the tip is deflected such that it is aligned with the cannula centerline or longitudinal axis 1418. The soft C-tip geometry does not reduce coring as well as the hard C-tip geometry of needle 1400 of the present invention.

The hard C-tip needle is manufactured according to the following process: Two-meter length of tubes are bundled and are cut to the cannula blank length. The ends of the tubes are de-burred and the tubes cleaned. The tubes are then automatically fed and automatically taped onto 18 inch grinding fixtures. The tubes on the grinding fixtures are placed on a grinding machine where a primary grind facet is applied. The tubes are then inclined and rotated to grind a second facet and inclined and rotated again to grind a third facet. The second and third facets are preferably symmetrical to one another. The cannula needle tip are rolled over to produce the curved hard "C" tip. The cannula are de-burred again and an anti-coring micro-blast is applied to the heel. The micro-blast may alternately be applied before bending. The cannula are electro or chemically polished then cleaned, dried, passivated and inspected before packaging. The cannula are packaged with the points/tips oriented in the same direction and wrapped in non-shedding paper to be placed in a polyethylene bag and into a foam line carton for distribution.

Figure 15:
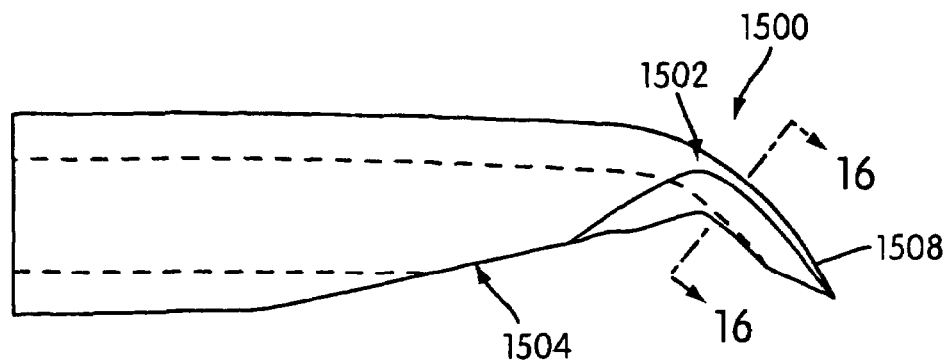
FIG. 15 is a longitudinal expanded sectional view of the forward end of the needle showing the front-ground geometry.
Figure 16:
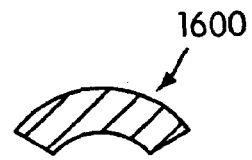
FIG. 16 is a sectional transversal view of the forward end of the needle showing the front-ground geometry.
Figure 17:
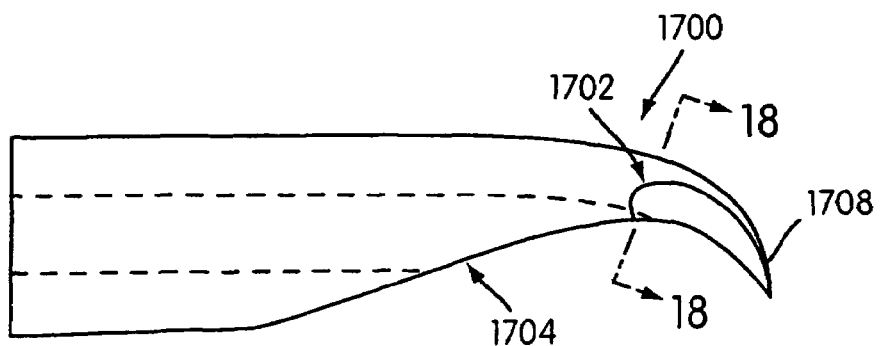
FIG. 17 is a longitudinal expanded sectional view of the forward end of the needle showing the back-ground geometry.
Figure 18:
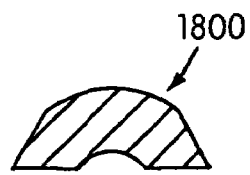
FIG. 18 is a sectional transversal view of the forward end of the needle showing the back-ground geometry.

All hypodermic needles have primary and secondary facets. The secondary facets are called lancets. FIG. 15 shows a sectional longitudinal view of a C-tip needle 1500. Lancets 1502 are shown in relation to the primary bevel 1504. A sectional transversal cut 16 of the tip 1508 is shown in FIG. 16 with a front ground where the tip 1508 is ground from the inside as shown on transversal cut 1600. FIG. 17 shows a sectional longitudinal view of a C-tip needle 1700. Lancets 1702 are shown in relation to the primary bevel 1704. A sectional transversal cut 18 of the tip 1708 is shown in FIG. 18 with a back ground where the tip 1708 is ground from the outside as shown on transversal cut 1800. Back-ground lancets bring advantages to a C-tip needle. An advantage is that the angled lancets may serve to further direct seal material away from the lumen. Another advantage is that the effectively narrower thus sharper leading edge may cut through clothing and skin or tissue more easily. The use of heavy-wall cannulas provides more wall thickness allowing a better optimization of the geometry of the back-ground lancets.

Figure 19:
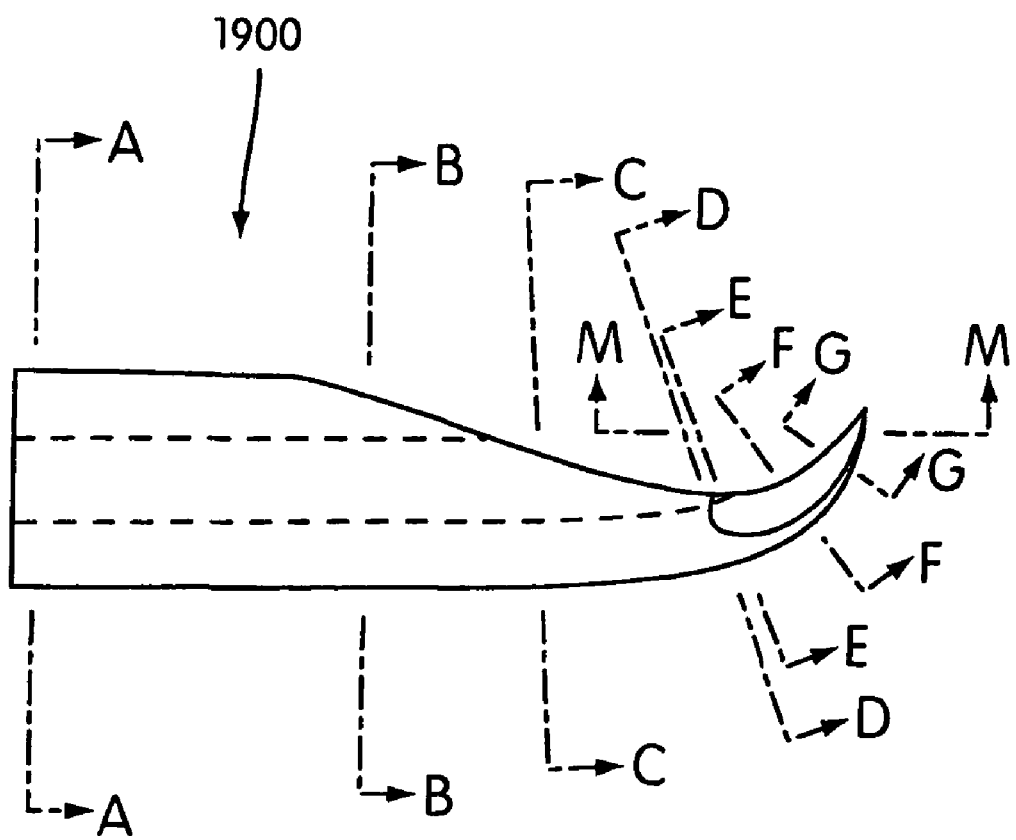
FIG. 19 shows the consecutive transversal sectional views of the forward end of the needle illustrating the back-ground geometry.
Figure 19A:
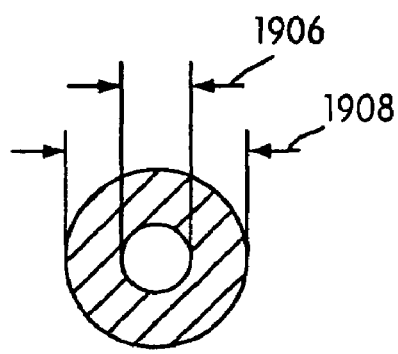
Figure 19B:
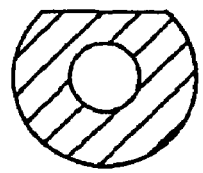
Figure 19C:
Figure 19D:
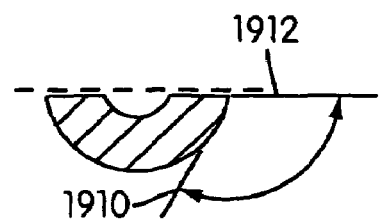
Figure 19E:
Figure 19F:
Figure 19G:
Figure 19M:

FIG. 19 shows the consecutive transversal cross sectional views of the needle tip 1900 in a case of a Hard-C tip needle with a back ground geometry. In one embodiment, the length of the needle is 1.343", the inside diameter 1906 is between 0.0138 inch and 0.0154 inch and the outside diameter 1908 is between 0.0280 and 0.0285. The tip 1900 is shown with consecutive transversal cross sectional views AA, BB, CC, DD, EE, FF, GG, MM displayed in FIGS. 19A, 19B, 19C, 19D, 19E, 19F, 19G and 19M. FIG. 19A shows the transversal cut AA having the shape of a disc corresponding to the tube/cylindrical form of the needle. Further along approaching the tip of the needle, FIG. 19D shows the cross-section DD with the back grinds 1910 at an angle of 120° in relation to the base line 1912. Other embodiments with a back grind with an angle of 130° are also within the scope of the present invention.

Figure 20:
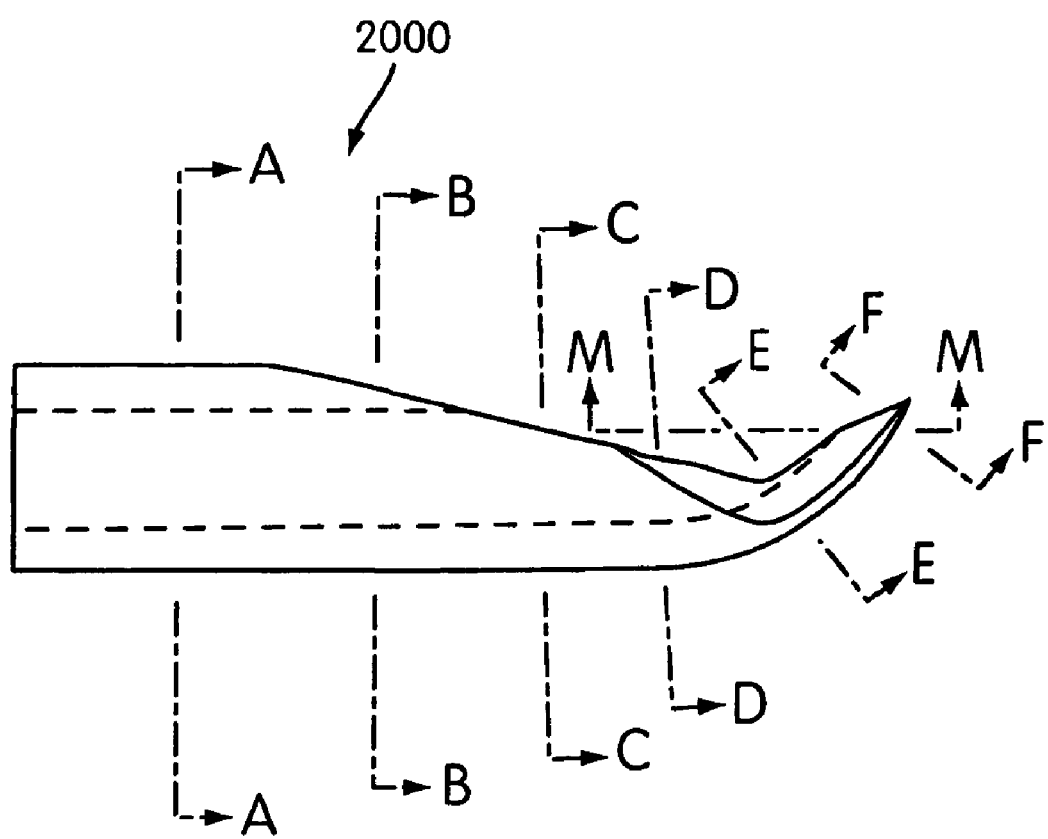
FIG. 20 shows consecutive transversal sectional views of the forward end of the needle illustrating the front-ground geometry.
Figure 20A:
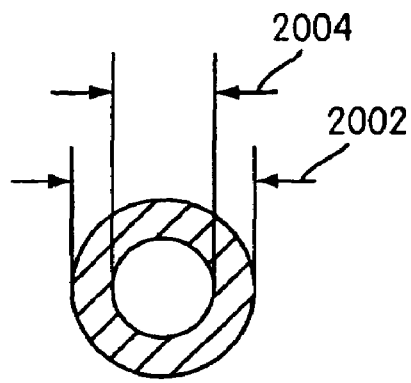
FIG. 20X shows a transversal sectional view of the forward end of the needle with a front-ground and back-ground geometry.
Figure 20B:
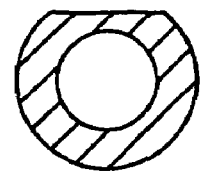
Figure 20C:
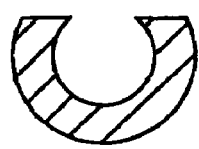
Figure 20D:
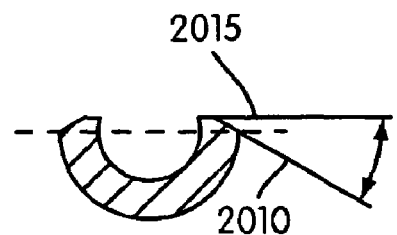
Figure 20E:
Figure 20F:
Figure 20M:
Figure 20X:
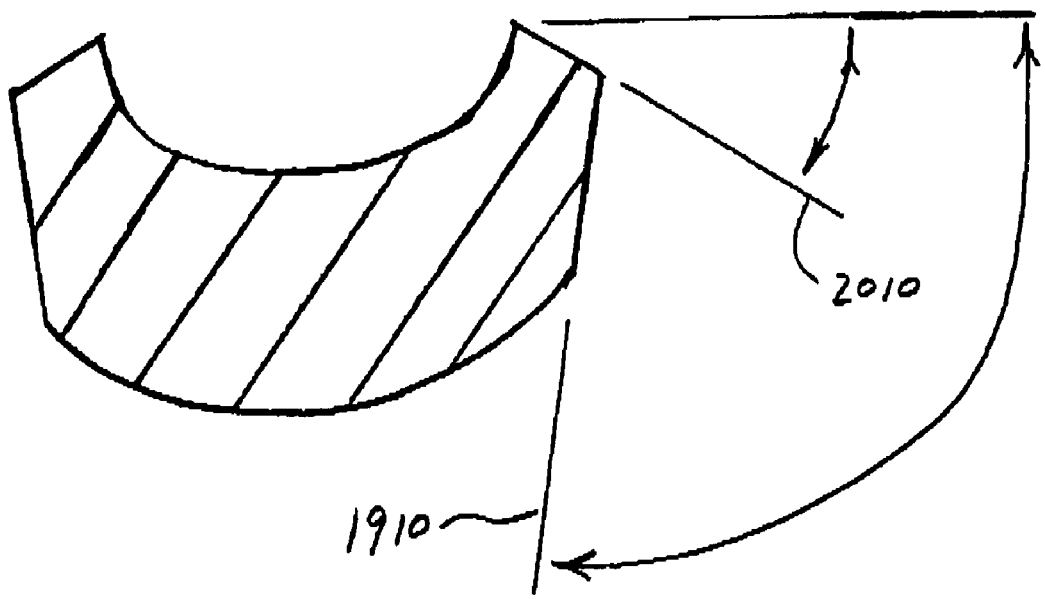

FIG. 20 shows the consecutive transversal cross sectional views of the needle tip 2000 in a case of a Hard-C tip needle with a front ground geometry. In one embodiment, the length of the needle is 1.343", the inside diameter 2002 is between 0.0155 inch and 0.0170 inch and the outside diameter 2004 is between 0.0280 and 0.0285. The tip 2000 is shown with consecutive transversal cross sectional views AA, BB, CC, DD, EE, FF, MM displayed in FIGS. 20A, 20B, 20C, 20D, 20E, 20F, 20M. FIG. 20A shows the transversal cut AA having the shape of a disc corresponding to the tube/cylindrical form of the needle, notice the cylindrical wall of the needle is thinner than in the previous embodiment. Further along approaching the tip of the needle, FIG. 20D shows cross-section DD with the front grinds 2010 at an angle of between about 250 and 35° and preferably 30° in relation to the base line 2015.

Tests show that the hard C-tip needle configuration can substantially eliminate coring when used in conjunction with softer springs that allow the tip of the needle to "flow" more easily inside the seal material. Combination of geometry elements for the C-tip such as back-ground geometry and hard C-tip configuration in conjunction with the use of softer springs, having a K spring constant between 1.5 lb/in and 6.5 lb/in, more preferably between 3 lb/in and 5 lb/in, provides enhanced performance of the needle in reducing coring.

Figure 21:
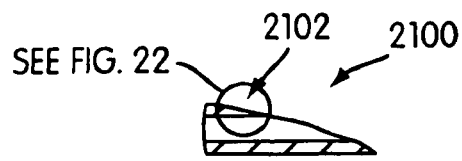
FIG. 21 is a longitudinal view of the forward end of the needle according to an alternative embodiment of the present invention where Parylene coating is applied to the needle.
Figure 22:
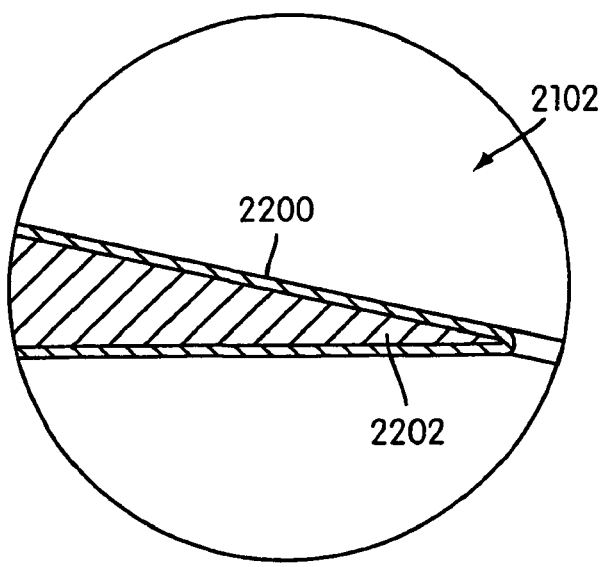
FIG. 22 is a longitudinal expanded view of the heel of needle according to embodiment illustrated in FIG. 21. The heel is shown uniformly coated with a conformal coating.

FIG. 21 shows a longitudinal sectional view of the needle tip 2100 coated with a conformal coating 2200 (shown in FIG. 22). A conformal coating is coating that conforms to the shape of the substrate while allowing blunting of sharp edges. In one embodiment, conformal coating 2200 consists of a Parylene coating (shown in FIG. 22). Parylene is a registered trademark of polyparaxylylene coating, manufactured by Specialty Coating Systems, Inc. of Indianapolis, Ind. The application of Parylene in coating an injection device and needle is described in U.S. Pat. No. 5,354,286 which is incorporated herein by reference. FIG. 22 shows a close up view of needle heel 2102. Membrane coring occurs when the needle heel 2102 cuts the outer surface of the seal. A rounded, or blunted, edge on the heel alleviates coring. Standard needles receive an abrasive blast during manufacturing however this blast is not sufficient since standard needles still create cores. Tests show that Parylene coating 2200 conforms well to the substrate geometry, including edges, for example edge 2202, as shown in FIG. 22.

selected between 13 to 18 degrees. The bend angle, that is the angle between a tangent to a curvature of the outer surface of the end tip of the needle and a longitudinal axis of the needle, is selected to be between 51° and 100°, preferably between 85° and 95°, most preferably 90° (FIG. 14 shows a bend angle of approximately 63° and FIG. 17 shows a bend angle of approximately 90°). The tip offset in relation to the wall of the needle is between 0.024 and 0.026 inches. The opening length is selected between 0.033 and 0.055 inches. The inside diameter is selected between 0.011 and 0.016 inches. The ratio length of opening to outside diameter of passage is between 1.7 to 2.2.

|  | Primary Angle (deg) | Bend Angle (tangent @ tip) (deg) | Opening Length (in) | Inside Diameter (in) | Ratio, L/OD | Tip Offset (in) |
|---|---|---|---|---|---|---|
| 10010 (Hard-C) | 14 | 63, 81 | .061 | .016 | 2.2 | .026 |
| 10014 (HC, Heavy Wall) | 13 | 51, 81 | .049 | .015 | 1.7 | .024 |
| 10017 (HC, HW, Back Ground) | 16.5 | 90, 90 | .063 | .015 | 1.9 | .024 |
| 10018 (HC, HW, BG, B-tip) | 13 | 90 | .053 | .011 | 1.9 | .024 |

Figure 23:
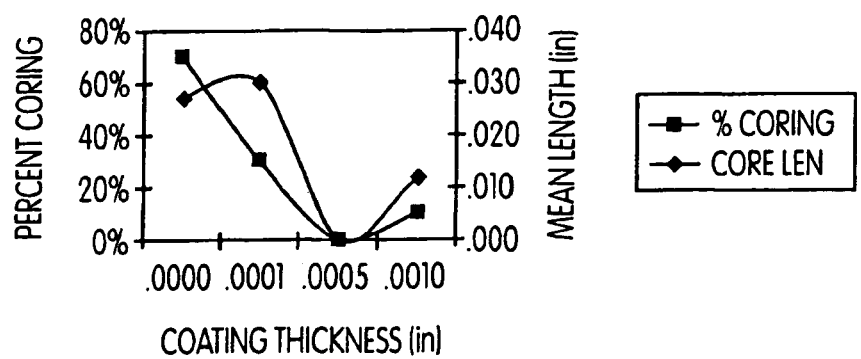
FIG. 23 is a graph showing the percentage of coring and the coring mean length versus the coating thickness as applied in embodiment illustrated in FIG. 22.

Parylene coating is applied at various thicknesses ranging from 0.0001 to 0.001 inch. Data collected in the study of effect of Parylene coating thickness on coring is summarized in graph shown in FIG. 23. The graph particularly shows that Parylene coating overall decreases the likelihood of coring as well as decreases the size of the core. However, as seen on the graph, increasing the coating thickness beyond around 0.0005" does not help in decreasing coring but acts in the opposite manner by increasing coring. Indeed, the graph in FIG. 23 clearly shows a curve minimum indicating that the optimum thickness of the coat accomplishing the desired results is a Parylene coating thickness around 0.0005". In addition, tests have shown that the use of a spring having a spring constant between 1.5 lb/inch and 6.5 lb/inch in conjunction with the use of a needle coated with Parylene is particularly beneficial in reducing coring.

Figure 24:
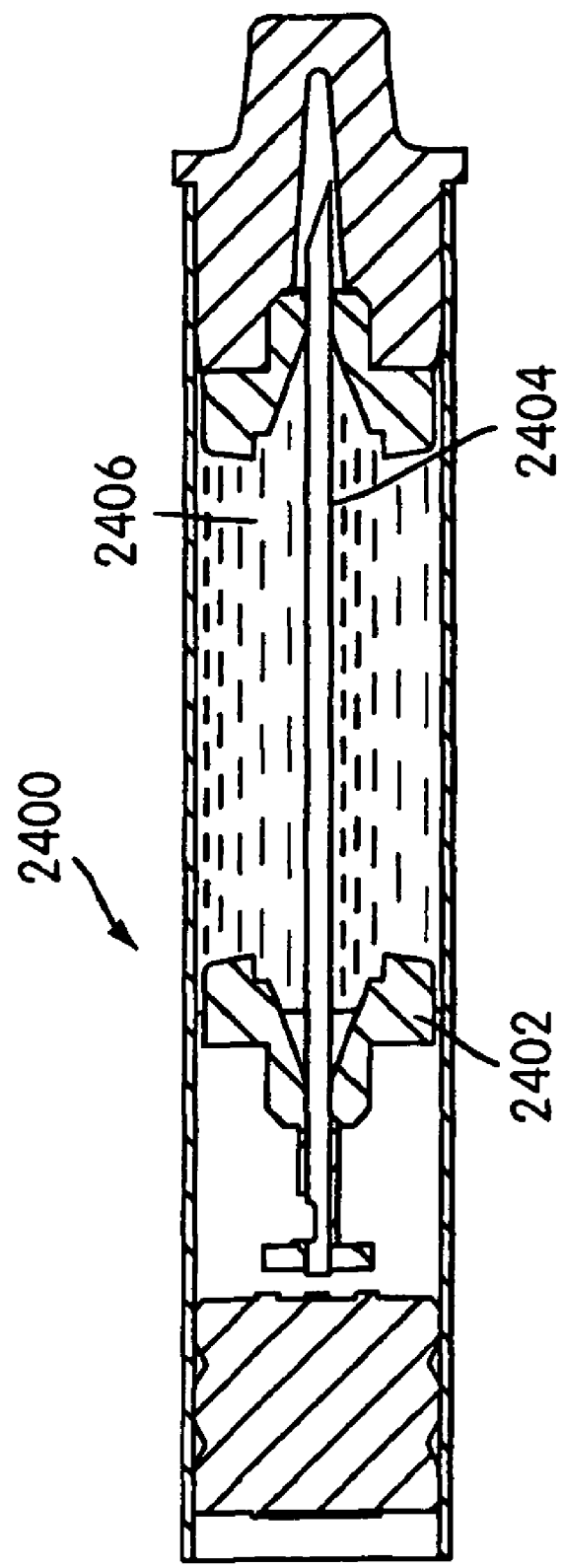
FIG. 24 is a longitudinal sectional view of an automatic injector according to another embodiment of the present invention.

FIG. 24 shows a longitudinal sectional view of a cartridge assembly 2400 used in an automatic injector according to another embodiment of the present invention. Automatic injector uses an alternative mechanism for reducing the rate of acceleration of the needle thus slowing down the speed of the needle in comparison with prior art devices. The acceleration rate is reduced so that the speed of the needle is less than 680 inches/s when the needle pierces the seal. The reduction in acceleration rate is intended specifically to reduce the speed to a level at which coring will not occur. Preferably, the speed at which the seal is pierced is also greater than 150 inches/s so that the injection operation is not delayed more than what is desirable. Indeed, damping disk 2402 attached to needle 2404 is used to reduce the rate of acceleration of needle 2404 by the friction generated when disk 2402 flows inside liquid medicament 2406. In other words, the flow resistance generated by the viscosity of the fluid liquid medicament against the movement of damping disk 2402 acts to reduce the rate of acceleration of needle 2404. Therefore, similarly to the previous embodiments, the damping disk plays the role of friction for slowing the tip of the needle, hence ultimately to substantially eliminating coring.

The Table below shows examples of geometries for various embodiments of the tip of the needle. The primary angle is While the invention has been described in connection with particular embodiments, it is to be understood that the invention is not limited to the disclosed embodiments, but on the contrary it is intended to cover various modifications and equivalent arrangements included within the spirit and scope of the invention as defined by the claims, which follow.

We claim:

1. An automatic injector comprising:
a housing having a rearward end and a forward end;
a seal structure disposed toward the forward end of said housing;
a cartridge contained within said housing;
a charge of medicament contained in said cartridge;
a plunger normally disposed in a generally rearward end of said cartridge and movable through said cartridge toward a generally forward end thereof in response to an actuating procedure, said movable plunger rearwardly confining said medicament within said cartridge;
a needle normally disposed within said housing, said needle being projectable from the forward end of said housing through said seal structure, said needle being communicable with said medicament so that movement of said plunger through said cartridge forces said medicament through said needle and into the flesh of an individual in response to said predetermined actuating procedure, said needle comprising:
a hollow rigid tubing having a cylindrical wall, the cylindrical wall having an inner surface and outer surface;
a lumen opening having a front pointed portion comprising a lancet shaped tip having a facet grinding at an angle, said tip bent in a curve directed toward a longitudinal axis of said cylindrical wall so as to shield the entire cross section of said lumen opening, said cross section of said lumen opening perpendicular to a longitudinal axis of said hollow rigid tubing, said tip comprising primary and secondary facets, said secondary facets ground at an angle at the inner surface of the needle; and
a releasable energy source releasable in response to said predetermined actuating procedure to project said needle from the forward end of the housing and slidingly drive said plunger through said cartridge in sealed relation to expel said medicament through said needle and into the flesh of an individual.

2. The automatic injector as claimed in claim 1, wherein said seal structure seals a forward end of said cartridge.

3. The automatic injector as claimed in claim 1, wherein said needle is normally stored within said cartridge, in contact with said medicament.

4. The automatic injector as claimed in claim 1, wherein said secondary facets are also ground at an angle at the outside surface of the needle.

5. The automatic injector as claimed in claim 1, wherein said releasable energy source comprises a normally compressed spring which is released in response to said predetermined actuating procedure.

6. The automatic injector as claimed in claim 1, wherein said spring having a spring constant between 1.5 lb/in and 6.5 lb/in.

7. The automatic injector as claimed in claim 1, wherein said seal structure comprises a material selected from the group of plastics and rubber.

8. The automatic injector as claimed in claim 1, wherein said friction area comprises a narrowed diameter portion in a wall of said cartridge.

9. The automatic injector as claimed in claim 8, wherein said plunger comprises ribs arranged to reduce the rate of acceleration of said needle when in contact with said friction region.

10. The automatic injector as claimed in claim 1, wherein said friction area is a corrugated portion in a wall of said cartridge.

11. The automatic injector as claimed in claim 10, wherein said plunger comprises ribs arranged to reduce the rate of acceleration of said needle when in contact with said friction region.

12. The automatic injector as claimed in claim 1, wherein a tip of said needle is coated with polyparaxylylene.

13. The automatic injector as claimed in claim 12, wherein said polyparaxylylene coating has a thickness between about 0.0001 to 0.001 inches.

14. The automatic injector as claimed in claim 1, wherein said plunger comprises a material selected from the group of plastics and rubbers.

15. The automatic injector as claimed in claim 14, wherein said plunger comprises a plurality of materials having different ductilities, said materials are selected to interact differently with said friction area to reduce the rate of acceleration of said needle.

16. An automatic injector comprising:
a housing having a rearward end and a forward end;
a seal structure disposed toward the forward end of said housing;
a cartridge contained within said housing;
a charge of medicament contained in said cartridge;
a plunger normally disposed in a generally rearward end of said cartridge and movable through said cartridge toward a generally forward end thereof in response to an actuating procedure, said movable plunger rearwardly confining said medicament with said cartridge;
a needle normally disposed within said housing, said needle being projectable from the forward end of said housing through said seal structure, said needle being communicable with said medicament so that movement of said plunger through said cartridge forces said medicament through said needle and into the flesh of an individual in response to said predetermined actuating procedure; said needle comprising:
a hollow rigid tubing having a cylindrical wall defining a longitudinal passage therethrough, said cylindrical wall including opposing first and second wall portions, said first wall portion having a forward tip portion terminating in a forward end tip, said second wall portion terminating at a position rearwardly spaced from said end tip, said forward tip portion being bent in a manner to shield the entire cross-section of said longitudinal passage, said cross section of said longitudinal passage perpendicular to a longitudinal axis of said hollow rigid tubing; and
a releasable energy source releasable in response to said predetermined actuating procedure to project said needle from the forward end of the housing and slidingly drive said plunger through said cartridge in sealed relation to expel said medicament through said needle and into the flesh of an individual.

17. The automatic injector as claimed in claim 16, wherein said seal structure seals a forward end of said cartridge.

18. The automatic injector as claimed in claim 16, wherein the tip of said needle is coated with polyparaxylylene.

19. The automatic injector as claimed in claim 18, wherein said polyparaxylylene coating has a thickness between about 0.0001 to 0.001 inches.

20. An automatic injector comprising:
a housing having a rearward end and a forward end;
a seal structure disposed toward the forward end of said housing;
a cartridge contained within said housing;
a charge of medicament contained in said cartridge;
a plunger normally disposed in a generally rearward end of said cartridge and movable through said cartridge toward a generally forward end thereof in response to an actuating procedure, said movable plunger rearwardly confining said medicament within said cartridge;
a needle normally disposed within said housing, said needle being projectable from the forward end of said housing through said seal structure, said needle being communicable with said medicament so that movement of said plunger through said cartridge forces said medicament through said needle and into the flesh of an individual in response to said predetermined actuating procedure; said needle comprising:
a hollow rigid tubing having a cylindrical wall defining a longitudinal passage therethrough, said cylindrical wall including opposing first and second wall portions, said first wall portion having a forward tip portion terminating in a forward end tip, said second wall portion terminating at a position rearwardly spaced from said end tip, said forward tip portion being bent in a manner to shield the entire cross-section of said longitudinal passage, said cross section of said longitudinal passage perpendicular to a longitudinal axis of said needle; wherein said forward tip portion is bent at an angle approximately between 51 degrees and 100 degrees; said angle being defined as the angle between a tangent to a curvature of an outer surface at said end tip and the longitudinal axis of said needle; and
a releasable energy source releasable in response to said predetermined actuating procedure to project said needle from the forward end of the housing and slidingly drive said plunger through said cartridge in sealed relation to expel said medicament through said needle and into the flesh of an individual.

21. The automatic injector as claimed in claim 20, wherein said seal structure seals a forward end of said cartridge.

22. An automatic injector comprising:
a housing having a rearward end and a forward end;
a seal structure disposed toward the forward end of said housing;
a cartridge contained within said housing;
a charge of medicament contained in said cartridge;
a plunger normally disposed in a generally rearward end of said cartridge and movable through said cartridge toward a generally forward end thereof in response to an actuating procedure, said movable plunger rearwardly confining said medicament within said cartridge;
a needle normally disposed within said housing, said needle being projectable from the forward end of said housing through said seal structure, said needle being communicable with said medicament so that movement of said plunger through said cartridge forces said medicament through said needle and into the flesh of an individual in response to said predetermined actuating procedure; said needle comprising:
  a hollow rigid tubing having a cylindrical wall defining a longitudinal passage therethrough, said cylindrical wall including opposing first and second wall portions, said first wall portion having a forward tip portion terminating in a forward end tip, said second wall portion terminating at a position rearwardly spaced from said end tip, said forward tip portion having a back ground lancet wherein back grinds of said lancet are ground at an angle of about 120 degrees measured in relation to a base line extending transversely across the forward tip portion, the forward tip portion being bent at an angle approximately between 51 degrees and 100 degrees; said angle being defined as the angle between a tangent to a curvature of an outer surface at said end tip and a longitudinal axis of said needle;
a releasable energy source releasable in response to said predetermined actuating procedure to project said needle from the forward end of the housing and slidingly drive said plunger through said cartridge in sealed relation to expel said medicament through said needle and into the flesh of an individual.

23. The automatic injector as claimed in claim 22, wherein said seal structure seals a forward end of said cartridge.

24. An automatic injector comprising:
a housing having a rearward end and a forward end;
a seal structure disposed toward the forward end of said housing;
a cartridge contained within said housing;
a charge of medicament contained in said cartridge;
a plunger normally disposed in a generally rearward end of said cartridge and movable through said cartridge toward a generally forward end thereof in response to an actuating procedure, said movable plunger rearwardly confining said medicament within said cartridge;
a needle normally disposed within said housing, said needle being projectable from the forward end of said housing through said seal structure, said needle being communicable with said medicament so that movement of said plunger through said cartridge forces said medicament through said needle and into the flesh of an individual in response to said predetermined actuating procedure; said needle comprising:
  a hollow rigid tubing having a cylindrical wall defining a linear longitudinal passage entirely there through, said cylindrical wall including opposing first and second wall portions, said first wall portion having a forward tip portion terminating in a forward end tip, said second wall portion terminating at a position rearwardly spaced from said end tip, said forward tip portion being bent in a manner to shield the entire cross-section of said longitudinal passage, said cross section of said longitudinal passage perpendicular to a longitudinal axis of said hollow rigid tubing; said needle comprising an enlarged rearward portion constructed and arranged for engagement with said plunger; and
a releasable energy source releasable in response to said predetermined actuating procedure to project said needle from the forward end of the housing and slidingly drive said plunger through said cartridge in sealed relation to expel said medicament through said needle and into the flesh of an individual.

25. The automatic injector as claimed in claim 24, wherein said seal structure seals a forward end of said cartridge.

26. An automatic injector comprising:
a housing having a rearward end and a forward end;
a seal structure disposed toward the forward end of said housing;
a cartridge contained within said housing;
a charge of medicament contained in said cartridge;
a plunger normally disposed in a generally rearward end of said cartridge and movable through said cartridge toward a generally forward end thereof in response to an actuating procedure, said movable plunger rearwardly confining said medicament within said carriage;
a needle normally disposed within said housing, said needle being projectable from the forward end of said housing through said seal structure, said needle being communicable with said medicament so that movement of said plunger through said cartridge forces said medicament through said needle and into the flesh of an individual in response to said predetermined actuating procedure; said needle comprising:
  a hollow rigid tubing having a cylindrical wall defining a linear longitudinal passage entirely there through, said cylindrical wall forming the boundary of the linear longitudinal passage, said cylindrical wall including opposing first and second wall portions, said first wall portion having a forward tip portion terminating in a forward end tip, said second wall portion terminating at a position rearwardly spaced from said end tip; said forward tip portion is bent at an angle approximately between 51 degrees and 100 degrees; said angle being defined as the angle between a tangent to a curvature of an outer surface at said end tip and a longitudinal axis of said needle; wherein said needle comprises an enlarged rearward portion constructed and arranged for engagement with said plunger;
a releasable energy source releasable in response to said predetermined actuating procedure to project said needle from the forward end of the housing and slidingly drive said plunger through said cartridge in sealed relation to expel said medicament through said needle and into the flesh of an individual.

27. The automatic injector as claimed in claim 26, wherein said seal structure seals a forward end of said cartridge.

28. An automatic injector comprising:
a housing having a rearward end and a forward end;
a seal structure disposed toward the forward end of said housing;
a cartridge contained within said housing;
a charge of medicament contained in said cartridge;

a plunger normally disposed in a generally rearward end of said cartridge and movable through said cartridge toward a generally forward end thereof in response to an actuating procedure, said movable plunger rearwardly confining said medicament within said cartridge;

a needle normally disposed within said housing, said needle being projectable from the forward end of said housing through said seal structure, said needle being communicable with said medicament so that movement of said plunger through said cartridge forces said medicament through said needle and into the flesh of an individual in response to said predetermined actuating procedure; said needle comprising:

a hollow rigid tubing having a cylindrical wall defining a longitudinal passage extending there through, said cylindrical wall having an inner surface and including opposing first and second wall portions, said first wall portion having a forward tip portion terminating in a forward end tip, said second wall portion terminating at a position rearwardly spaced from said end tip, said forward tip portion being bent;

an enlarged rearward portion constructed and arranged for engagement with said plunger, and a lumen opening having a front pointed portion comprising a lancet shaped tip having a facet grinding at an angle, said forward tip bent in a curve directed toward a longitudinal axis of said cylindrical wall so as to constitute a shield to said lumen opening, said tip comprising primary and symmetrical secondary and tertiary facets, said secondary and tertiary facets each ground at the outside surface of the needle at an angle ranging from 120 degrees to 130 degrees measured in relation to a base line extending transversely across the forward tip portion; and a releasable energy source releasable in response to said predetermined actuating procedure to project said needle from the forward end of the housing and slidingly drive said plunger through said cartridge in sealed relation to expel said medicament through said needle and into the flesh of an individual.

29. The automatic injector as claimed in claim 28, wherein said seal structure seals a forward end of said cartridge.

30. An automatic injector comprising:
a housing having a rearward end and a forward end;
a seal structure disposed toward the forward end of said housing;
a cartridge contained within said housing;
a charge of medicament contained in said cartridge;
a plunger normally disposed in a generally rearward end of said cartridge and movable through said cartridge toward a generally forward end thereof in response to an actuating procedure;
a needle normally disposed within said housing, and projectable from the forward end of said housing through said seal structure, said needle being communicable with said medicament so that movement of said plunger through said cartridge forces said medicament through said needle in response to said predetermined actuating procedure, said needle comprising:

a hollow rigid tubing having a cylindrical wall that includes opposing first and second wall portions, said first wall portion having a forward tip portion terminating in a forward end tip, said second wall portion terminating at a position rearwardly spaced from said end tip, said forward end tip portion having a back ground lancet wherein back grinds of said forward end tip portion are at an angle ranging from 120 degrees to 130 degrees in relation to a base line extending transversely across the forward tip portion; and a releasable energy source releasable in response to said predetermined actuating procedure to project said needle from the forward end of the housing and slidingly drive said plunger through said cartridge to expel said medicament through said needle and into the flesh of an individual.

31. A method of injecting a medicament with an automatic injector, the injector comprising a housing, a seal structure disposed toward a forward end of said housing, a cartridge contained within said housing, a charge of medicament contained in said cartridge, a plunger movable through said cartridge toward a generally forward end thereof in response to an actuating procedure, a needle disposed within said housing and having a linear longitudinal passage entirely through the needle, said needle projectable from the forward end of said housing through said seal structure, said needle communicable with said medicament so that movement of said plunger through said cartridge forces said medicament through the longitudinal passage of said needle in response to said actuating procedure, a releasable energy source responsive to said actuating procedure to project said needle from the forward end of the housing and slidingly drive said plunger through said cartridge to expel said medicament through said needle; said method comprising:

releasing said energy source;
forcing said medicament through said linear longitudinal passage of said needle;
moving said needle forwardly within said housing at a speed of less than 680 inches/s as said needle penetrates said seal structure;
penetrating said seal structure with said needle having a forward tip portion bent so as to shield the entire cross-section of the longitudinal passage, said cross section of the longitudinal passage perpendicular to a longitudinal axis of said needle; and
expelling said medicament through said needle.

32. The method as recited in claim 31, wherein said moving said needle forwardly within said housing comprises moving said needle at a speed of more than 150 inches/s as said needle penetrates said seal structure.

* * * * *

UNITED STATES PATENT AND TRADEMARK OFFICE
CERTIFICATE OF CORRECTION

PATENT NO.      : 7,569,035 B1                                       Page 1 of 1
APPLICATION NO. : 09/985466
DATED           : August 4, 2009
INVENTOR(S)     : Wilmot et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1643 days.

Signed and Sealed this

Seventh Day of September, 2010

David J. Kappos
*Director of the United States Patent and Trademark Office*